US011049600B2

(12) United States Patent
Jones

(10) Patent No.: US 11,049,600 B2
(45) Date of Patent: Jun. 29, 2021

(54) SYSTEM AND METHOD FOR PROVIDING DRUG LIBRARY DATA TO A MEDICAL DEVICE LOCATED WITHIN A HEALTHCARE ENVIRONMENT

(71) Applicant: Fresenius Vial SAS, Brezins (FR)

(72) Inventor: Alaster Jones, Saint Sauveur (FR)

(73) Assignee: Fresenius Vial SAS, Brézins (FR)

( * ) Notice: Subject to any disclaimer, the term of this patent is extended or adjusted under 35 U.S.C. 154(b) by 864 days.

(21) Appl. No.: 14/765,114

(22) PCT Filed: Feb. 24, 2014

(86) PCT No.: PCT/EP2014/053549
§ 371 (c)(1),
(2) Date: Jul. 31, 2015

(87) PCT Pub. No.: WO2014/131729
PCT Pub. Date: Sep. 4, 2014

(65) Prior Publication Data
US 2015/0371004 A1      Dec. 24, 2015

Related U.S. Application Data

(60) Provisional application No. 61/769,958, filed on Feb. 27, 2013.

(30) Foreign Application Priority Data

Feb. 27, 2013   (EP) .................................... 13305225

(51) Int. Cl.
*G06F 19/00*     (2018.01)
*G16H 20/17*     (2018.01)
(Continued)

(52) U.S. Cl.
CPC .............. *G16H 20/17* (2018.01); *G16H 40/67* (2018.01); *G16H 70/40* (2018.01)

(58) Field of Classification Search
CPC ........ G06F 19/00; G16H 20/17; G16H 40/67; G16H 70/40
(Continued)

(56) References Cited

U.S. PATENT DOCUMENTS 6,327,535 B1 * 12/2001 Evans ...................... G01S 1/68
701/300
8,051,414 B2    11/2011 Stender et al.
(Continued)

FOREIGN PATENT DOCUMENTS

| CN | 1493049 | 4/2004 |
| CN | 1759398 | 4/2006 |

(Continued)

OTHER PUBLICATIONS

Richard Swim, "Deployment of an Enterprise Wireless Infusion Pump Management System," IT Horizons, 2008, pp. 29-32 (Year: 2008).*

(Continued)

*Primary Examiner* — Joshua B Blanchette
(74) *Attorney, Agent, or Firm* — Cook Alex Ltd.

(57) ABSTRACT

A system for providing drug library data to a medical device (31, 32) located within a healthcare environment, the system comprises a local network (33) of the healthcare environment (3) and at least one medical device (31, 32) for administering a drug to a patient, the at least one medical device (31, 32) being located in the healthcare environment (3) and connected to the local network (33). Herein, a drug library server (1) is connected to the local network (3) of the healthcare environment (3) via a public communication network (2) and constituted to provide drug library data to (Continued)

the at least one medical device (31, 32) via the public communication network (2). In this way, a system and method for providing drug library data to a medical device located within a healthcare environment is provided which allows for an easy creation, editing and sharing of drug library data for use and distribution between medical devices within a particular healthcare environment and across different healthcare environments.

11 Claims, 16 Drawing Sheets

(51) Int. Cl.
  *G16H 40/67* (2018.01)
  *G16H 70/40* (2018.01)
(58) Field of Classification Search
  USPC .......................................... 705/2, 3
  See application file for complete search history.

(56) References Cited

U.S. PATENT DOCUMENTS

| | | | | |
|---|---|---|---|---|
| 9,135,393 | B1* | 9/2015 | Blomquist | G06F 19/3468 |
| 2002/0083342 | A1* | 6/2002 | Webb | H04L 67/2814 |
| | | | | 726/12 |
| 2002/0169636 | A1 | 11/2002 | Eggers et al. | |
| 2004/0128162 | A1 | 7/2004 | Schlotterbeck et al. | |
| 2005/0108057 | A1 | 5/2005 | Cohen et al. | |
| 2005/0137653 | A1* | 6/2005 | Friedman | A61B 5/0002 |
| | | | | 607/60 |
| 2005/0246416 | A1 | 11/2005 | Blomquist | |
| 2006/0026205 | A1 | 2/2006 | Butterfield | |
| 2007/0233520 | A1 | 10/2007 | Wehba et al. | |
| 2007/0233521 | A1* | 10/2007 | Wehba | G16H 40/67 |
| | | | | 705/3 |
| 2008/0091466 | A1* | 4/2008 | Butler | G06Q 10/06 |
| | | | | 705/2 |
| 2012/0065990 | A1 | 3/2012 | Howard et al. | |
| 2013/0191513 | A1* | 7/2013 | Kamen | G16H 40/67 |
| | | | | 709/219 |
| 2013/0221084 | A1* | 8/2013 | Doss | H04L 63/0492 |
| | | | | 235/375 |

FOREIGN PATENT DOCUMENTS

| | | | |
|---|---|---|---|
| CN | 101044487 | 9/2007 | |
| JP | 2007-507046 | 3/2007 | |
| JP | 2007-528241 | 10/2007 | |
| JP | 2010-507176 | 3/2010 | |
| JP | 2010-264255 | 11/2010 | |
| JP | 2012-187411 | 10/2012 | |
| WO | WO2003/094090 | 11/2003 | |
| WO | WO2005/036447 | 4/2005 | |
| WO | WO-2005036447 A2 * | 4/2005 | ........... G06F 19/327 |
| WO | WO2010/132617 | 11/2010 | |
| WO | WO-2010132617 A2 * | 11/2010 | ........... A61B 5/7465 |

OTHER PUBLICATIONS

Lor Siv-Lee et al., "Implementation of Wireless "Intelligent" Pump IV Infusion Technology in a Not-for-Profit Academic Hospital Setting," Hospital Pharmacy vol. 42, No. 9, pp. 832-840 (Year: 2007).*
Siv-Lee et al., "Implementation of Wireless 'Intelligent' Pump IV Infusion Technology in a Not-for-Profit Academic Hospital Setting", Hospital Pharmacy, vol. 42, No. 9, pp. 832-840 (Sep. 1, 2007).
International Search Report and Written Opinion, counterpart International Appl. No. PCT/EP2014/053549 (dated Sep. 26, 2014).
Search Report, counterpart Chinese App. No. 201480010644.7 (dated Apr. 11, 2017) (2 pages).
First Office Action with English translation, counterpart Chinese App. No. 201480010644.7 (dated Apr. 27, 2017) (22 pages).
Second Office Action with English translation, counterpart Chinese App. No. 201480010644.7 (dated Sep. 25, 2017) (24 pages).
Fourth Office Action with English translation, counterpart Chinese App. No. 201480010644.7 (dated Mar. 4, 2019) (8 pages).
Notification to Grant Patent Right with English translation, counterpart Chinese App. No. 201480010644.7 (dated May 20, 2019) (3 pages).
Search Report with English translation, counterpart Japanese App. No. 2015-559477 (dated Jan. 30, 2018) (32 pages).
Notice of Reasons for Refusal with English translation, counterpart Japanese App. No. 2015-559477, (dated Feb. 20, 2018) (8 pages).
Decision to Grant a Patent with English translation, counterpart Japanese App. No. 2015-559477, (dated Oct. 9, 2018) (5 pages).

* cited by examiner

SYSTEM AND METHOD FOR PROVIDING DRUG LIBRARY DATA TO A MEDICAL DEVICE LOCATED WITHIN A HEALTHCARE ENVIRONMENT

The present application is a U.S. National Stage of PCT International Patent Application No. PCT/EP14/53549, filed Feb. 24, 2014, which claims the benefit of U.S. Provisional Appl. No. 61/769,958, filed Feb. 27, 2013, and priority to EP Application No. 13305225.8, also filed Feb. 27, 2013, all of which are hereby incorporated herein by reference.

The invention relates to a system for providing drug library data to a medical device located within a healthcare environment according to the preamble of claim 1 and a method for providing drug library data.

A system of this kind comprises a local network of the healthcare environment and at least one medical device for administering a drug to a patient. The at least one medical device is located in the healthcare environment and is connected to the local network.

Typically, medical devices for administering a drug to a patient, such as infusion pumps, are installed at various locations in a healthcare environment, for example in a hospital facility. Such medical devices may for example be located in different rooms of wards (care units) of a hospital or in operating rooms. Nowadays, such medical devices are connected to a local network for communicating with a hospital management system hosted on a server located in the healthcare environment. For example, a group of infusion pumps may be installed on a rack serving as a communication link to the local network such that via the rack the infusion pumps are connected to the local network and are operative to communicate with a hospital management system on a server within the healthcare environment, for example within a hospital, via the local network, for example a local area network (LAN) or a wireless local area network (WLAN).

To control the operation of medical devices of this kind for administering drugs to a patient, so called drug libraries are installed on such medical devices, a drug library comprising drug library data characterizing a drug, its ingredients, rules for compatibility and rules for administration or the like. A drug library may for example comprise a list of drugs in which each drug is associated with parameters defining for example boundary values for administration by means of an infusion device. Such boundary values may for example relate to a minimum and maximum dosage for administering a particular drug, a minimum and maximum rate for administering a drug, a minimum and maximum time of administration and the like. In addition, such boundary values may be dependent on the age, weight and gender of a patient and, hence, may be patient-specific.

By using such drug libraries the operation of a medical device such as an infusion pump for administering a particular drug to a patient is controlled in that the medical device may be operated by a nurse only within the boundaries posed by the drug library. For this, for administering a drug to a patient, the nurse identifies the drug to the medical device, upon which the medical device automatically loads the respective rules and boundary values from a drug library installed on the medical device.

Presently, such drug libraries are locally installed within a healthcare environment, for example within a hospital. Such drug libraries are for example installed as software on a personal computer (PC) or a server within a hospital, from which the drug library may be distributed to medical devices located in different wards of a hospital in order to be installed on such medical devices.

With systems presently used it is cumbersome to distribute drug library software within a healthcare environment and, in particular, to keep drug library software up to date throughout the entire healthcare environment. This may lead to multiple variants of drug libraries being used within a healthcare environment, for example within a particular hospital, posing a risk for safety due to the possibility of multiple references of drug libraries with possibly inconsistent data.

Furthermore, at present it is impossible to easily share drug libraries between different healthcare environments, for example between different hospitals. A sharing of drug libraries between different hospitals (possibly belonging to a common healthcare group such as a hospital carrier) in this regard may be beneficial because a large part of drug parameterization is common between hospitals and stereotyped by patient demographics (in particular age, weight and gender of a patient). Current systems hence pose a hurdle for a standardization of parameterization of drugs.

WO 2005/036447 A2 discloses a medication management system including a medication management unit associated with a medical device. The medication management unit is set up to compare a medication order information from a first input means to machine readable delivery information from a second input means and to download a medication order to the medical device only if the information from the first input means matches the information from the second input means. The medication management unit also comprises a drug library editor enabling a user to import, export and edit whole drug libraries and individual drug library values to control and customize a drug library according to hospital preferences.

From WO 2010/132617 A2 a computer-implemented method of interacting with a medical device in conjunction with a user device is known. Within the method a certified medical application is received at a user device and is stored in a secure memory segment. A communication link is established from the user device to the medical device in order to execute the certified medical application on the medical device.

It is an object of the instant invention to provide a system and method for providing drug library data to a medical device located within a healthcare environment which allows for an easy creation, editing and sharing of drug library data for use and distribution between medical devices within a particular healthcare environment and across different healthcare environments.

This object is achieved by a system comprising the features of claim 1.

Accordingly, a drug library server is provided which is connected to the local network of the healthcare environment via a public communication network and is constituted to provide drug library data to the at least one medical device via the public communication network.

The instant invention is based on the idea to provide a web based service for providing drug library data. Drug library data herein is contained and stored on a drug library server located within a public communication network such as the internet. By means of a web based service it becomes possible to allow users to create drug libraries online and to easily share drug library data between medical devices within a particular healthcare environment and across different healthcare environments. It furthermore becomes possible to create, share and map external information such as information from external data bases such as the U.S.

National Library of Medicine to medical devices. By means of such a web based service drug libraries within a healthcare environment and across several healthcare environments can easily be managed, allowing for an easy distribution and updating of drug library data.

In the context of this text a drug library is to be understood as a list of drugs in which each of the drugs is associated with parameters defining operational boundaries for administering the particular drug to a patient. Such parameters may depend on the patient demographics, for example the patient's age, weight or gender.

Furthermore, in the context of this text a local network shall be understood as a non-public communication network (also referred to as intranet), in this regard being distinguished from a public communication network such as the internet.

A healthcare environment may be for example a healthcare institution such as a hospital. A hospital typically has a certain number of wards each having multiple patient bedrooms. A healthcare environment may, however, also be a group of several hospitals belonging to a single healthcare group, for example being run by a single hospital carrier using a common local network (intranet).

Within the healthcare environment different medical devices for administering drugs to patients may be present. The medical device may for example be an infusion pump such as a syringe pump or a volumetric pump. The medical devices may origin from a single manufacturer or from different manufacturers.

The medical device may also be constituted as a rack to which one or multiple infusion pumps can be connected. The rack in this case serves as a communication link for carrying the infusion pumps and for connecting them to the local network for communication with a hospital management system of the healthcare environment. In this case, both the rack and the infusion pumps form medical devices to which drug library data may be installed (drug library data may for example be installed on a rack for distribution to infusion pumps connected to the rack).

The system allows for an easy creation, editing and sharing of drug libraries by providing a web based service. The system herein may comprise one or multiple communication devices comprising a web client for communicating with the drug library server via the public communication network, for example via the internet. The communication devices may be constituted by personal computers (PC), notebook computers, personal digital assistants (PDAs), mobile phones or any other device allowing for a connection to the internet. Via such a communication device a user may connect to the drug library server to create a drug library, edit drug library data and manage the sharing of a created drug library.

In particular, the system is constituted to allow a user, by means of a communication device, to access the drug library server via the public communication network to create and share a drug library, create and share a configuration, the configuration herein defining operational rules of medical devices, create and share a care area, the care area corresponding to a combination of a configuration and a drug library and being assigned to a subarea (for example a ward) within the healthcare environment (for example a hospital), and/or create and share a data set, the data set representing a group of care areas, hence mapping the structure of a healthcare environment such as a hospital.

A user may in addition be also allowed to for example publish data created by means of pre-defined collaboration mechanisms to outside a hospital environment.

By accessing the drug library server over the public communication network, for example the internet, a user may manage drug libraries to be used in a healthcare environment and manage its distribution and sharing properties. A user herein may via the internet be allowed to edit his personal settings, to edit collaboration settings to allow for a sharing of drug library data between different users, care units, hospital facilities or health care groups to define the distribution of drug libraries within a particular hospital by defining care units relating to subareas such as wards of a hospital or to create a complete data set mapping the entire drug library structure of a hospital or even a group of hospitals. In addition to drug library data the user herein can also set configuration data relating to medical devices such as infusion pumps, such configuration data being contained in a so called configuration and setting operational rules for a medical device for example to customize a display area of the medical device or to define parameters of particular security features.

The drug library server is located within the public communication network and hence in the public domain, for example in the internet domain. The medical devices, in contrast, are located in the local network and hence in a non-public, private domain confined to the particular healthcare environment. The drug library server (in the public domain) hence is not able to freely communicate with the medical devices located within the non-public environment of the local network and hence cannot as such easily obtain information for example regarding the localization of medical devices within a particular healthcare environment. For transferring drug library data and also other, for example configuration data to the medical devices, however, it must be known where in the local network the medical devices are located in order to identify them for example by means of their network address (for example by means of their so called IP address). For this purpose, the drug library server may provide a device discovery tool to be executed by a communication device within a particular healthcare environment in order to gather information about medical devices being installed within the healthcare environment (for example from an asset tracking system or a local service distribution point device table). The device discovery tool may be provided on the drug library server for download to a communication device. It also is conceivable, however, that a communication device is enabled to execute the device discovery tool being installed on the drug library server without downloading the underlying software. By executing the device discovery tool on the communication device within a particular healthcare environment, then, information can be gathered about medical devices being installed within the particular healthcare environment, and such information may be uploaded to the drug library server such that the drug library server obtains localization information about the medical devices within the local network of the healthcare environment.

The device discovery tool may be operative to scan the local network of a particular healthcare environment for medical devices connected to it in order to identify their respective address in the network (hence to obtain their network address). The device discovery tool furthermore may be operative to extract information, for example from log files of a rack carrying infusion pumps, about infusion pumps currently or previously installed to the rack. From the log files the device discovery tool for example may recognize when a particular infusion pump has been connected or disconnected from a particular rack. An alternate method is to use the pump internal history file recording selected care area usage markers. By uploading such information to the drug library server and by analyzing the information and associating it with localization data of the rack stored on the drug library server, then, the movement of an infusion pump within a care unit or a hospital facility may be tracked. The localization data of the rack may for example identify in which room of which ward within a care unit in a hospital facility a rack is installed, such that it can be derived at what time an infusion pump has been used at such location when it is known at what time the infusion pump has been connected to the rack.

If the localization of a medical device is known from execution of the device discovery tool, or from an asset tracking system, it also becomes possible to automatically assign a care area to the medical device based on the known localization of the medical device. A care area in this regard may relate to a care unit of a hospital facility and is associated with a certain combination of drug library and configuration. By automatically assigning a predefined care area to a medical device dependent on its localization the medical device hence is caused to use a particular drug library when installed and used within the care unit associated with that care area.

By means of the device discovery tool, in addition, also a maintenance tracking, a tracking of the software status and an error logging can be performed to provide statistical data on the usage of medical devices.

Furthermore, based on localization data of a medical device obtained by means of the device discovery tool a barcode identifying the medical device may be generated, printed and attached to the medical device containing at least one unique identifying piece of data. For the barcode generation an online tool to create a so called QR code can be used, also known as QR code API (API: Application Programming Interface). The information contained in the barcode may serve to identify the location of the medical device within the healthcare environment (for example by using a unique identifier and exchange with a real time location tracking service to obtain for example the bed number, the bedroom number, the ward name, the care unit name and the hospital facility name) and the identification within the local network (providing for example the IP address). By means of the discovery tool a barcode for identifying and localizing a medical device can in an easy-to-use fashion be created, printed and attached to a medical device such that an identification of the medical device, for example an infusion pump, may easily be carried out for example by a nurse when a drug is to administered by means of the medical device.

A barcode identifying the medical device (and being generated in the above stated manner or in any other known manner) may also be used to facilitate the transferring of drug library data to the medical device. For this, a communication device such as a smart device (such as a smart phone) or another portable device located within the healthcare environment and connected to the local network may be operative to scan a barcode attached to a medical device in order to identify the medical device. By means of the barcode, a communication link to a communication interface (for example a web interface) of the medical device may be established in order to transfer data to the medical device via such communication interface.

For this, in a first step drug library data may for example be downloaded from the drug library server to the communication device. In a second step, the communication device reads a barcode of the medical device on which the drug library data is to be installed and, via the barcode, the communication device is directed to a communication interface (for example a web interface) of the medical device. Via the communication interface then the drug library data is transferred to the medical device and in this way installed on the medical device.

It also is conceivable to directly install drug library data from the drug library server to a particular medical device. However, by using the detour via the communication device and the web interface of a medical device it can be made sure that no update of software of the medical device is carried out while the medical device is in operation administering a drug to a patient.

In an alternative approach, rather than using a communication device and a web interface for transferring drug library data to the medical device, an internal distribution server located within the local network of the healthcare environment may be used. For example, the internal distribution server may receive a message from the drug library server whenever new drug library data related to a medical device in the local network is available. Such new data is then downloaded from the drug library server to the internal distribution server, wherein the internal distribution server may be constituted to archive previous data for purposes of traceability and logging of the data. The distribution server comprises a list of all medical devices located within the local network of the healthcare environment. Whenever a medical device such as an infusion pump connects to the local network, the internal distribution server verifies the medical device against its list, checks the version of the drug library data installed on the medical device and its compatibility with new data, and if the new data is compatible it transfers the new drug library data to the medical device.

Additionally, the internal distribution server may comprise a web server implemented on the internal distribution server, wherein the web server communicates and relays information about the status of transactions relating to one or multiple medical devices, such that for example the versions of drug library data currently installed on a medical device may be checked via the web server.

If drug library data shall be transferred to multiple infusion pumps being connected to a rack, the above outlined procedure may be used to first transfer the drug library data to the rack. The rack may then distribute the drug library data to the infusion pumps connected to the rack in a separate step, possibly prompted by the communication device such that a distribution of the drug library data to the attached infusion pump is only carried out upon an explicit command from the communication device.

The drug library server advantageously could output its drug library data in a common XML or JSON/BSON format (XML: Extensible Mark-up Language; JSON: Java Script Object Notation; BSON: Binary JSON) or alternatively in a secure proprietary data format. By outputting drug library data in a commonly known and accepted format a drug library server of this kind may be used in connection with medical devices of different manufacturers by providing an output which is readable independent on the specific preferences and settings of a certain manufacturer installation. The medical device is responsible for checking the integrity of data and validating the content against its own operating set of rules.

The object is also achieved by a method for providing drug library data to a medical device located within a healthcare environment. The method comprises the step of installing drug library data on at least one medical device for administering a drug to a patient, the at least one medical device being located in a healthcare environment and connected to a local network of the healthcare environment. Within such method the drug library data is provided to the at least one medical device by a drug library server connected to the local network of the healthcare environment via a public communication network.

The advantages and advantageous embodiments described above with regard to the system according to the invention are equally applicable also to the noted method such that it in this regard shall be referred to the above description.

The idea underlying the invention shall subsequently be described in more detail with reference to the embodiments shown in the figures. Herein, FIG. 1 shows a schematic overview of a system for providing a drug library data to a medical device;

Figure 1:
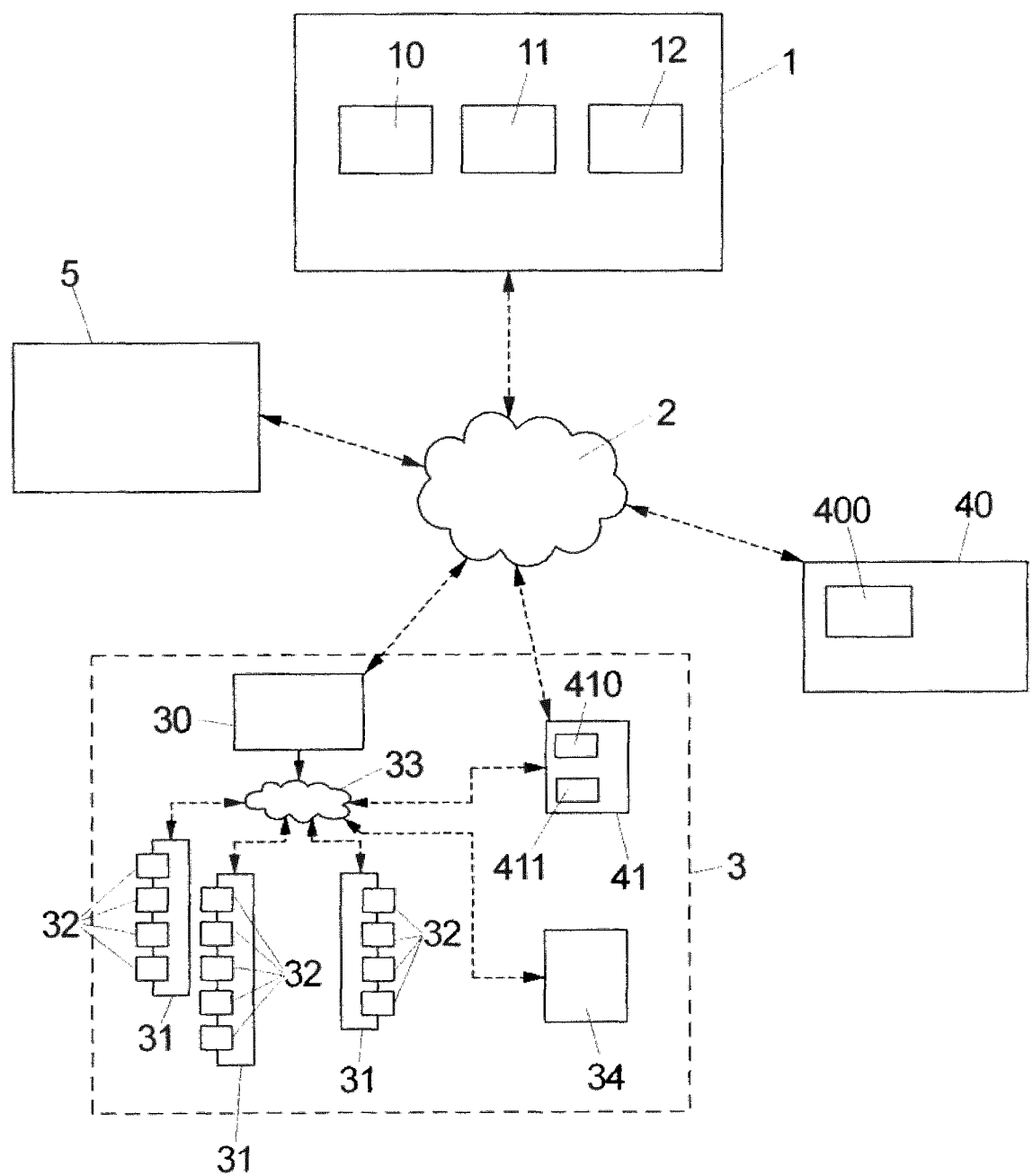
FIG. 1 shows a schematic overview of a system for providing drug library data to medical devices 31, 32, located within a healthcare environment 3.

A healthcare environment 3 in this regard may be for example a hospital. The hospital may be organized to have different clinics, departments, wards (care units) and operation facilities and the like. Throughout the hospital, a number of medical devices 31, 32 may be distributed serving to administer drugs to patients. Such medical devices may be infusion pumps 32 connected to racks 31, wherein the racks 31 serve as mechanical carriers for the infusion pumps 32 on the one hand and as communication links to facilitate communication between the infusion pumps 32 and a hospital local network 33 on the other hand. Via the racks 31 and the local network 33 (for example set up as a local area network (LAN)) the infusion pumps 32 may be connected to a hospital management system, hence, allowing for a centralized management of the infusion pumps 32 within the hospital local network 33.

The system as depicted in FIG. 1 provides a web-based service for providing drug library data to medical devices 31, 32. Drug libraries, as they are conventionally known, serve to provide rules to medical devices 31, 32 for administering drugs to a patient. In particular, drug libraries in the context of infusion devices 32 contain a list of drugs in which each drug is associated with parameters that define, characterize and impose boundary values on an infusion device 32 for administering the particular drug to a patient. For example, such boundary values may relate to the dosage, the rate of administration and the time of administration for a drug and may vary for different drugs and also for different types of patients, for example dependent on the age, weight and gender of a patient.

The drug libraries are installed on the medical devices 31, 32, in particular on the infusion pumps 32, such that during operation of an infusion pump 32 parameters set by the drug library for a certain drug are applied. For example, a nurse is not enabled to choose a dosage rate outside a range of dosage rates defined by the applied drug library for a certain drug. If a certain drug is to be administered to a patient, a nurse can choose administration parameters only within the boundaries defined by the drug library.

Commonly, drug libraries are locally installed on a computer within the healthcare environment 3, for example, within a hospital management system and are distributed locally to the medical devices 31, 32. This makes it cumbersome to distribute new or updated drug libraries throughout an entire healthcare environment 3 without having duplicate variants of drug libraries being installed on different medical devices 31, 32.

By providing a web-based service for providing drug library data, this problem is overcome in that a drug library server 1 is provided within a public domain. The drug library server 1 can be connected via a public communication network 2, for example the internet, to a communication interface 30, for example a router, within the healthcare environment 3 or can be connected directly to a local communication network 33. In case of connection to a public communication network 2, the drug library server 1 can interact with medical devices 31, 32 or a distribution server 34 trough hospital network equipment (for example the communication interface 30 such as a router within the healthcare environment 3). In case of direct connection to a local network 33, the drug library server 1 can directly interact with medical devices 31, 32 or the distribution server 34. In both cases, the drug library server 1 can interact with external services 5 through the public communication network 2. The drug library server 1 hosts a web server 10, a communication interface (web interface components interface) 11 and a data base components interface 12.

Via the web server 10, the drug library server 1 provides data to web clients 400, 410 on communication devices 40, 41, constituted for example as portable devices, such as PDAs or portable computers.

The web interface components interface 11 provides an interface for interaction with an (internal or external) distribution server 34 and/or directly to the medical devices 31, 32 by means of, for example, the Hypertext Transfer Protocol (HTTP). The web interface components interface 11 exists on the hosted service, which is the creation point for the data on the drug library server 1. The data export route from the drug library server 1 to the medical devices 31, 32 is either through a VPN connection to a local distribution point in the healthcare environment 3, or data can be downloaded to a communication device 40, 41 such as a smart device, PC or laptop and then transferred internally from the communication device 40, 41 to one or multiple medical devices 31, 32. The web interface route in the local healthcare environment 3 could be from a distribution server 34 to a care area server, a rack (column) 31 or an infusion device (pump) 32. This all depends on the infrastructure of the hospital etc. and its IT capacity.

The database components interface 12 provides access to databases containing drug library data and other data relating to medical devices 31, 32 to be provided within the web-based service.

The web-based service provided by means of the drug library server 1 shall serve to support medical devices 31, 32, in particular infusion devices, of a particular manufacturer or universally for different manufacturers. The drug library server 1 herein shall run database components combining the product knowledge and evolutions, client management and accounts, product services and sales. The drug library server 1 shall allow for a creation, uploading, downloading and/or managing of drug libraries online within a managed client space, wherein a client space may relate to an entire hospital, a particular service or to an individual user. The web based service allows for an import or export of drug libraries to arbitrary communication devices 40, 41 such as mobile devices, smart devices, PCs or laptop computers or the like which can access the drug library server 1 via web clients 400, 411. The drug library server 1 furthermore may contain specific tools available for download, such tools facilitating the managing of medical devices 31, 32.

By means of the web-based service a service centred architecture is provided. The service allows for an easy upgrade and evolution of software components. The drug library server 1 holds client accounts, contacts, status reporting and management centrally. This alleviates an installation in a local healthcare environment domain such as a hospital. The centralized service also allows for a centralized product control and licensing and also allows, for the service operator, to perform a targeted marketing, to obtain usage statistics and to provide targeted usage services. By means of the drug library server 1 drug libraries can be easily created and shared online in a standardized way, wherein templates may be available for the creation of a drug library. By means of the web-based service the distribution and upgrading to keep drug libraries within a particular healthcare environment 3 and even across several healthcare environments 3 up to date is greatly facilitated.

Figure 2:
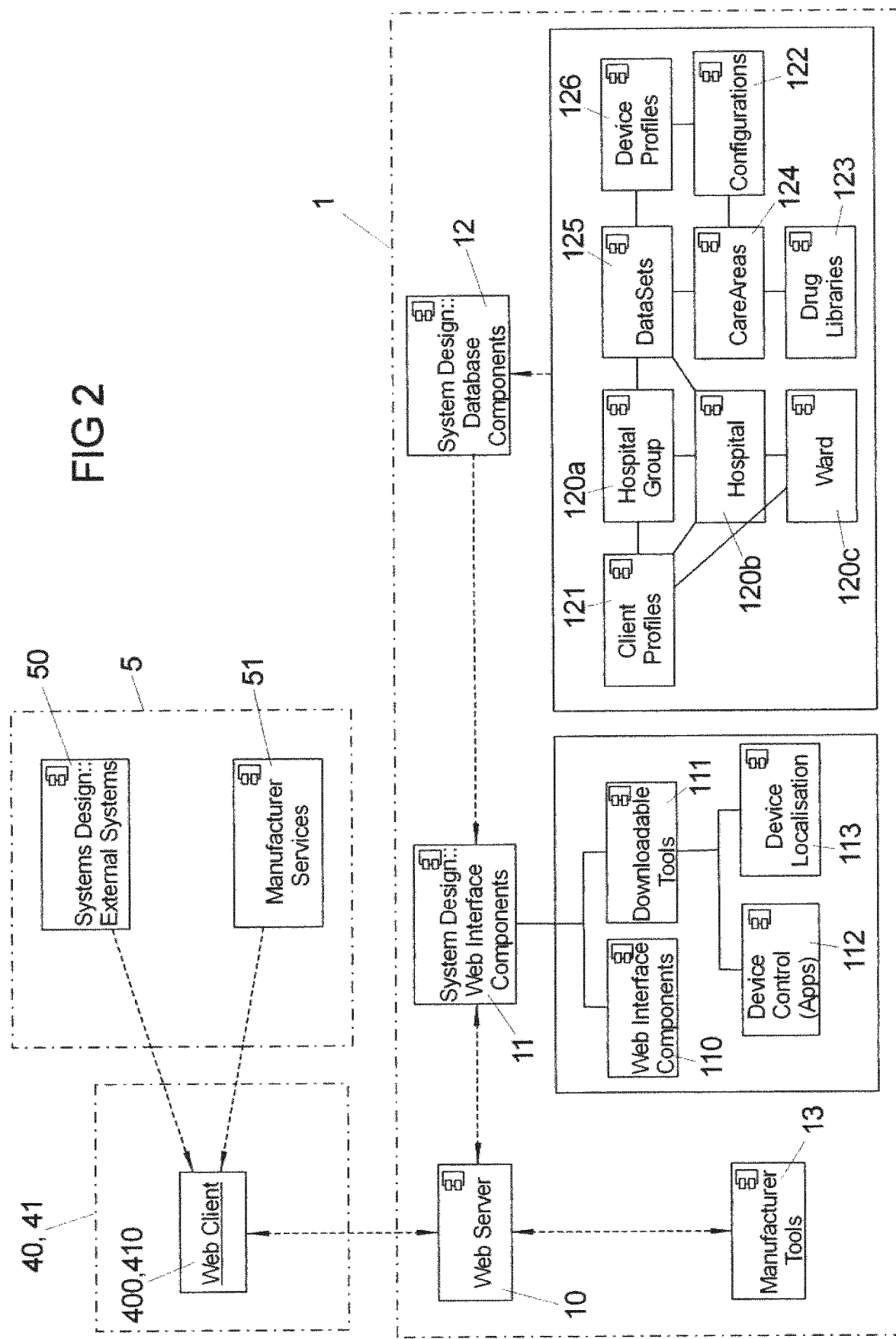
FIG. 2 shows a schematic overview of a drug library server of the system.

FIG. 2 shows a schematic overview of the drug library server 1. As already noted, the drug library server 1 holds a web server 10, a web interface components interface 11 and a database components interface 12. Via the web server 10 the drug library server 1 communicates with web clients 400, 410 of communication devices 40, 41, for example arbitrary mobile devices having a connection to the public communication network 2, for example the internet. Via the web server 10 a user can access the web interface components interface 11 and the database components interface 12.

The web interface components interface 11 provides access to a file system containing resources such as web interface components 110 and downloadable tools 111. The downloadable tools may for example be device control applications 112 (so-called apps) or a device localization tool 113.

The database components interface 12 provides access to various databases containing data with regard to client profiles 121 associated with a hospital group 120a, a hospital 120b and/or a ward (care unit) 120c, configurations 122, drug libraries 123, care areas 124, data sets 125 and device profiles 126.

In addition, the drug library server 1 may contain manufacturer tools 13 provided for download to communication devices 40, 41. Among such tools may for example be a device discovery tool facilitating the localization of medical devices 31, 32 within a healthcare environment 3, as shall be described in more detail below.

The web-based service may also interact and make use of external services 5 such as services provided by external systems 50 (external to a particular device manufacturer) or services of a particular device manufacturer (manufacturer services 51). By means of the external services 5 a user may map external information (for example from other data bases such as the U.S. National Library of Medicine) to medical devices 31, 32. External services 50 as U.S. National Library of Medicine can be used by the drug library server 1 or by the internal distribution server 34 to automatically or manually import data and transform the data to a dataset which is distributable and understandable by medical devices 31, 32. Manufacturer services 51 can be used by the drug library server 1 or by the internal distribution server 34 to automatically or manually import a dataset which is distributable and understandable by medical devices 31, 32. In both case, a user can interact with the drug library server 1 or with the internal distribution server 34 to import, modify and export datasets.

According to FIGS. 3 to 16, subsequently the creation, sharing and transferring of profiles and data within the web based service shall be described in more detail.

Figure 3:
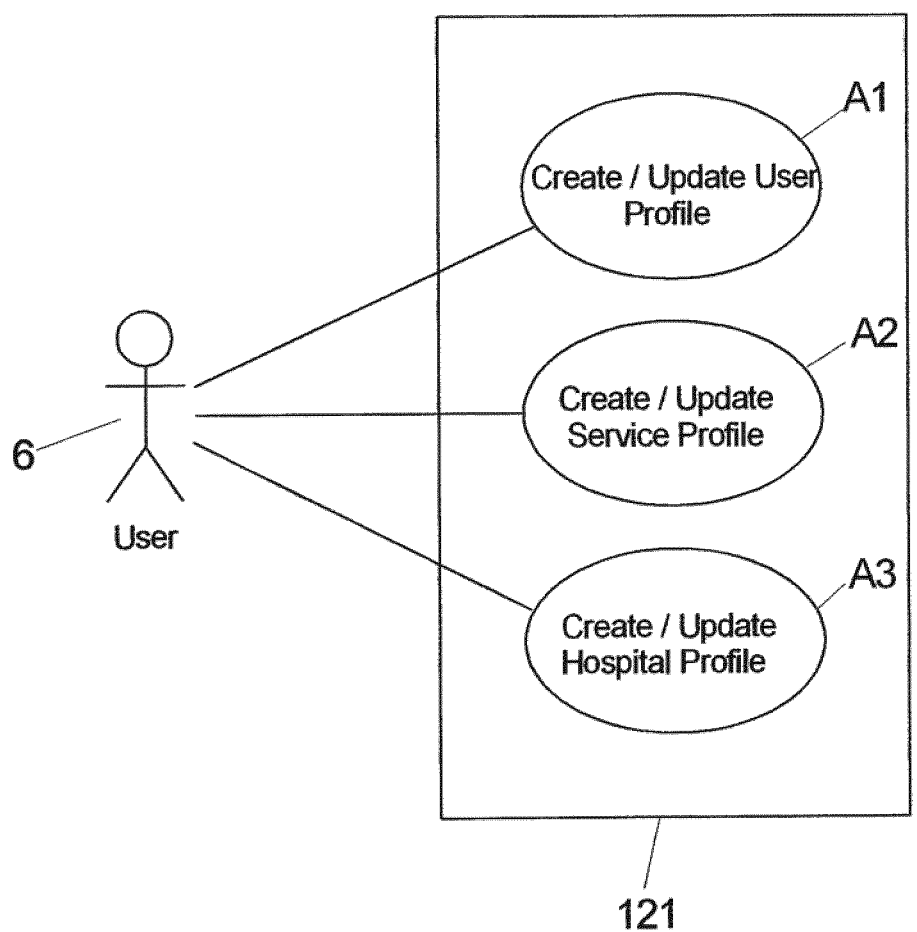
FIG. 3 shows a schematic overview of a functionality to create a user profile within a web based service for providing drug library data.

As shown in FIG. 3, a user 6 may, within the web based service provided by the drug library server 1, create and update user profiles (A1), create and update service profiles (A2) and create and update hospital profiles (A3). Such profiles relate to an individual user (A1), to a care unit (A2) or to an entire hospital (A3) or to a hospital trust. Within a user profile, for example, a name, an e-mail address, a position, a service and a hospital may be specified. Within a care unit profile, different users belonging to a particular care unit may be specified (A2). Once a user is added to the service profile, its user profile is made public to other users of the care unit, possibly depending on privacy control settings of the user and a care unit. A hospital profile may for example specify different care units and/or users belonging to the hospital (A3). The care units specified within the hospital profile are public to each other.

Accessing the drug library server 1 a user 6 may freely create profiles or change data relating to a profile. For this, a user 6 may access the drug library server 1 by using a user name and a password. By means of an arbitrary communication device 40, 41, for example a PDA (smart device) or another mobile device, the user 6 herein can access the drug library server 1 from anywhere, provided he has access to the public communication network 2, for example the internet.

Figure 4:
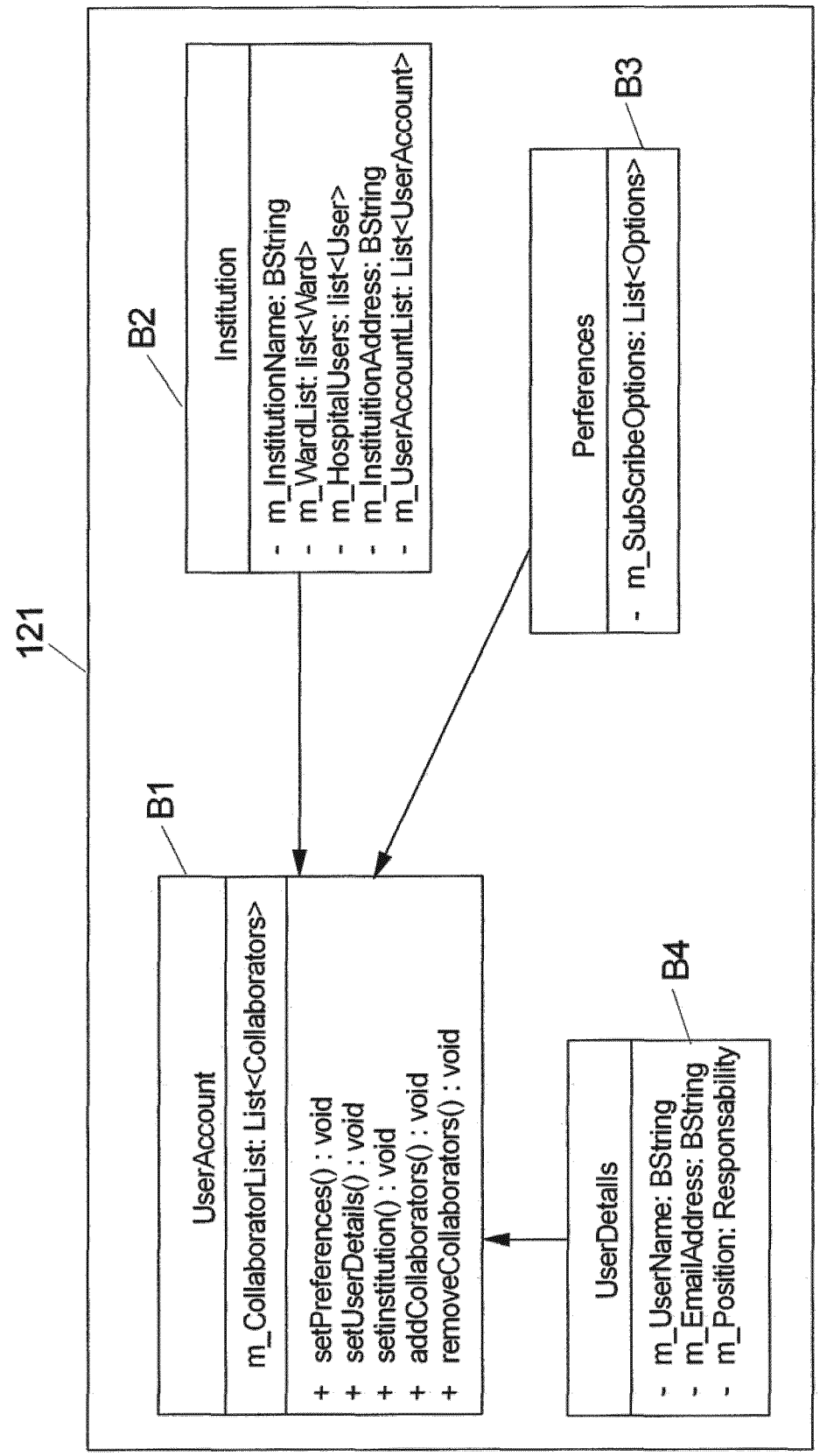
FIG. 4 shows a schematic overview of a user account.

As shown in FIG. 4, a user account (B1) relating to a particular user 6 may comprise data concerning user preferences (B3), to user details such as a user name, an e-mail address or a position of the user within a particular healthcare environment 3 (B4) and an institution (in the US referred to as "facility") (B2). The institution herein may be defined by its name, by a list of care units, by users belonging to that institution, by a postal address of the institution and by a list of user accounts associated with that institution.

Figure 5:
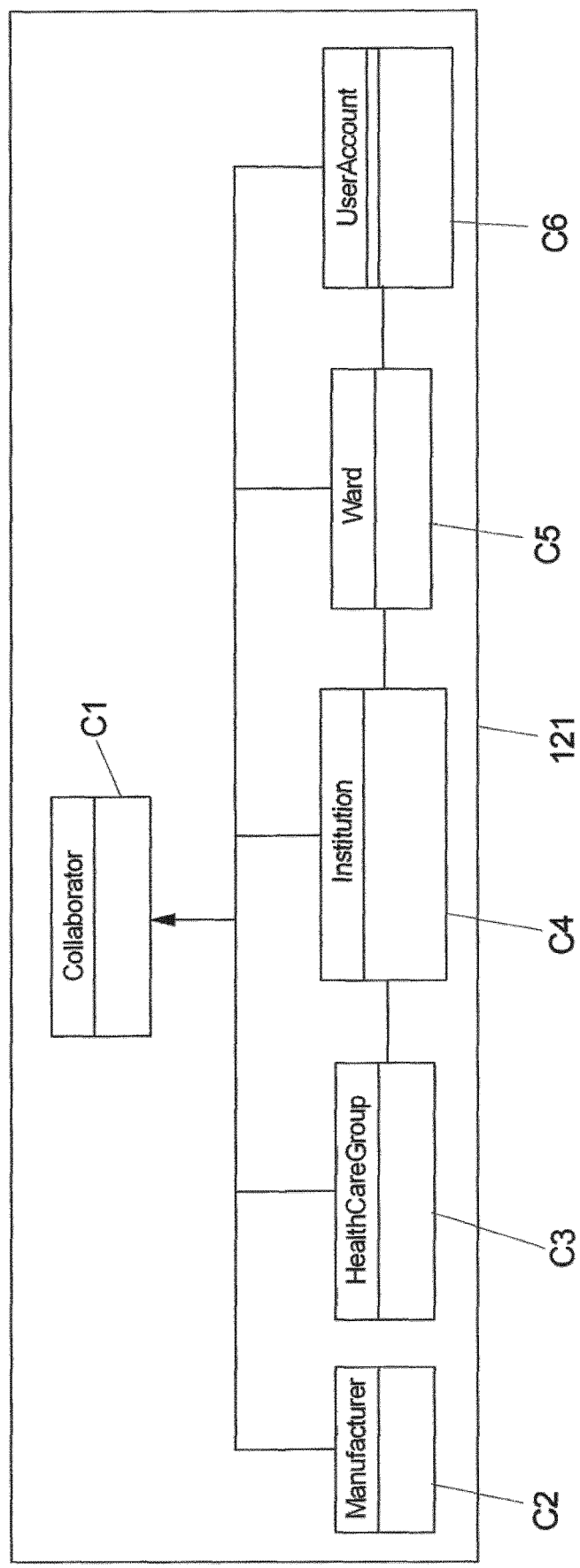
FIG. 5 shows a schematic overview of a collaboration setting within a web based service for providing drug library data.

The user account (B1) may furthermore comprise a list of so called collaborators (C1). As schematically shown in FIG. 5, a user 6 may specify collaborating entities such as users (C6), care units (C5), institutions (C4) or entire healthcare groups (C3). Such collaboration settings may be used for example to easily share data between the collaborators in that all collaborating entities are automatically informed for example once an update of a drug library is available such that drug libraries can easily be kept current throughout all collaborating entities. A user account (C6) may for example be set to collaborate with a care unit (C5), an institution (C4) and/or an entire healthcare group (C3), wherein the healthcare group (C3) may comprise several hospitals collaborating with each other. Also, a collaboration with a manufacturer may be defined (C2). The manufacturer herein may define a role of pre-created drug libraries. By adding a manufacturer to the collaborators' list, newly created drug libraries or updates of drug libraries originating from the manufacturer may be distributed throughout the collaborating entities.

In this regard, a user account 6 can be attached to different level of hierarchies which may affect its capacity to share data. For example, a chief pharmacist of a health care group comprising several hospitals may be attached to a profile of a type "Health Care Group" and may hence be enabled to publish data to all hospital facilities belonging to a particular health care group. A hospital pharmacist of a particular hospital may have a profile of a type "Hospital" and would not be able to publish data to all hospitals within a health care group, but only within a particular hospital. A hospital pharmacist may for example take data published by a chief pharmacist and adapt it to the specific facility settings. This mechanism drills down to a care unit and ward level such that users associated with a profile of type "Care Unit" are allowed to publish data only throughout a particular care unit.

Figure 6:
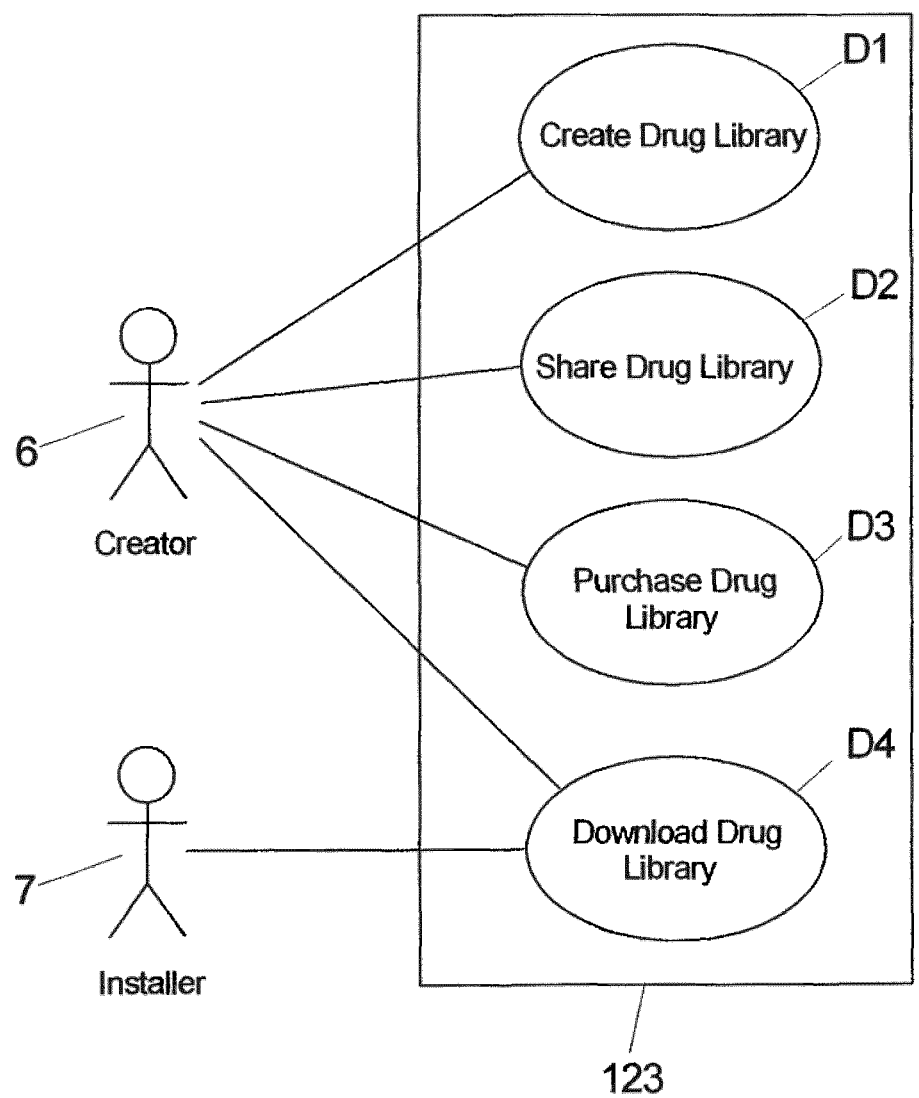
FIG. 6 shows a schematic overview of a drug library creation within a web based service for providing drug library data.
Figure 7:
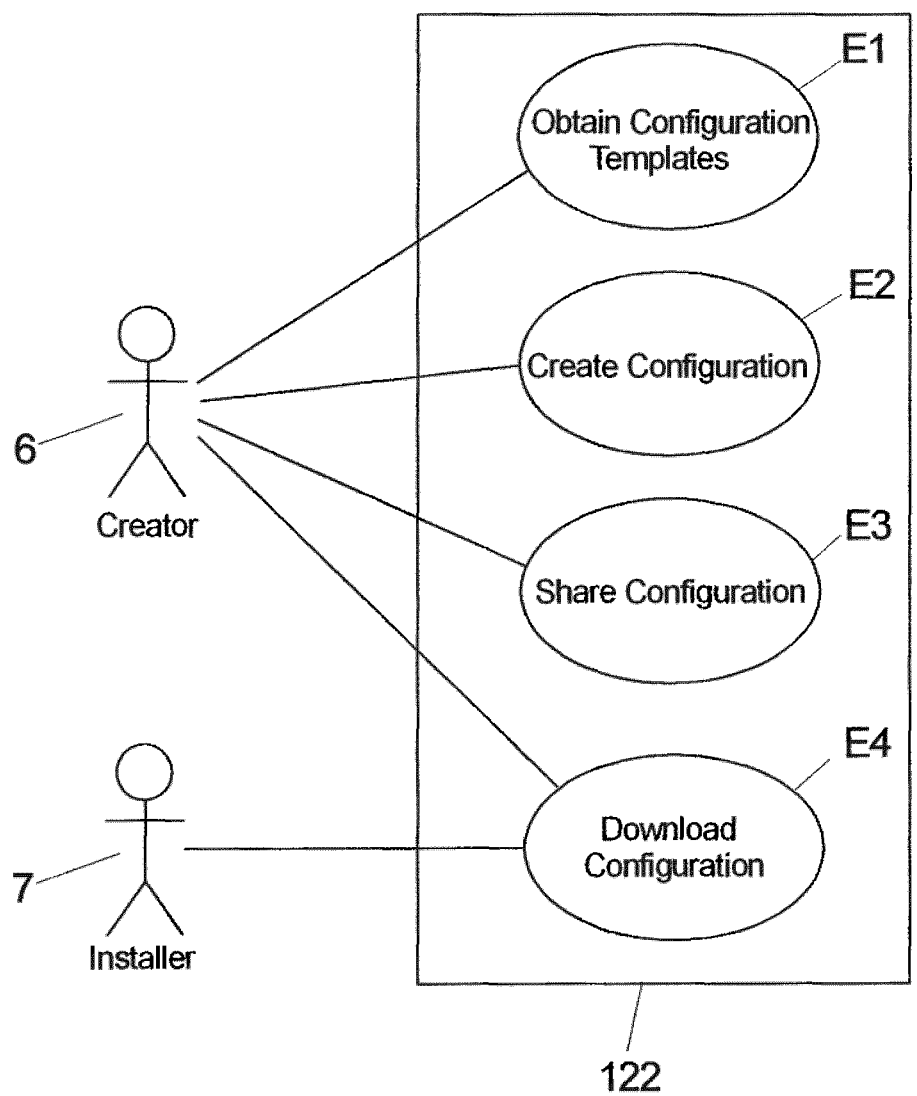
FIG. 7 shows a schematic overview of a configuration creation within a web based service for providing drug library data.

As shown in FIG. 6, a user 6 may create a drug library (D1), may share a drug library (D2), may purchase a drug library (D3) or may download a drug library (D4). In addition, the user 6 may connect to external services 5 (see FIGS. 1 and 2) to map external information, for example information available from other manufacturers or providers of drugs regarding for example compatibilities, syringe and dilutions, to drug libraries.

A user 6 may create an entirely new drug library or he may share an existing drug library with other users. Furthermore, he may purchase a drug library (D3) from external drug library creators. For creating or editing a drug library, a user 6 accesses the drug library server 1 using his user name and password and is directed to his personal client space in which he is displayed the drug libraries he is associated with. Within the client space he is allowed to create, edit, manage, purchase and share drug libraries.

Drug libraries are to be installed on medical devices to facilitate the administering of drugs to patients. For this, an installer 7 may download drug libraries from the drug library server 1 to transfer drug library data to medical devices 31, 32. The installer 7 may be different from a user (creator) 6 creating a drug library. In particular, an installer 7 may be allowed to download drug libraries of other users 6 which he is not allowed to edit.

How the transfer of drug library data to medical devices 31, 32 may be achieved shall be described in more detail below.

A user 6 may furthermore create a so called configuration. A configuration herein is a set of rules applied to medical devices 31, 32. Parameters defined in a configuration may for example serve to customize a display area of a respective medical device 31, 32 or may define settings for security features of such medical device 31, 32.

A user 6 may obtain a configuration template (E1), may create a configuration (E2), may share a configuration (E3) or may download a configuration (E4). Templates herein should be available to creators using the knowledge base of the web based service housed on the drug library server 1. The medical device 31, 32, for example an infusion pump 32, is for example described in this context by its product type and software version. Manufacturing data based on unique identifiers such as product number or serial number herein may be referenceable to a user 6 in order to obtain a correct customization template. A configuration may be downloaded by an installer 7 for installing configuration data on medical devices 31, 32.

Figure 8:
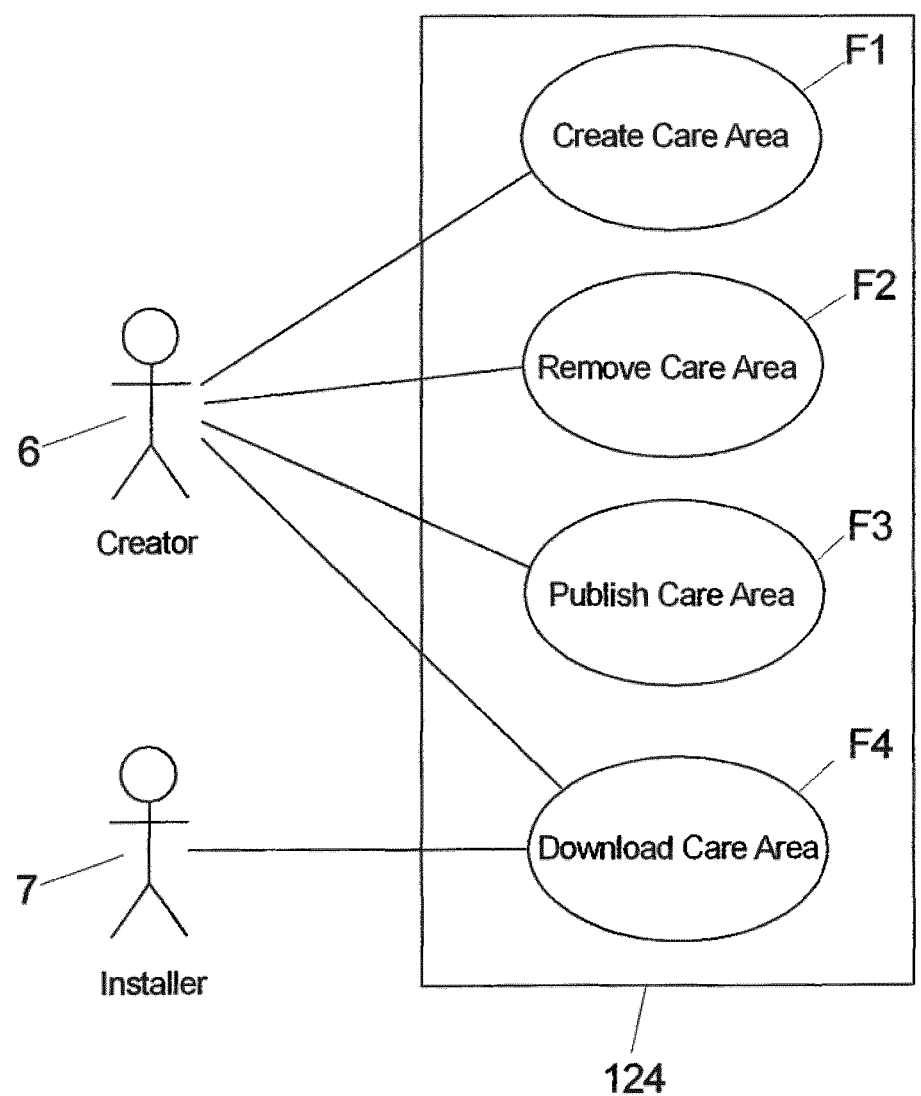
FIG. 8 shows a schematic overview of a care area creation within a web based service for providing drug library data.

As shown in FIG. 8, a user 6 may furthermore create a so called care area (F1), may remove a care area (F2), may publish a care area (F3) or may download a care area (F4). A care area herein is a combination of a configuration and a drug library and may relate to a sub area of the healthcare environment 3, for example a ward of a hospital. By means of the care area it is possible to for example associate particular combinations of configurations and drug libraries with medical devices 31, 32 arranged in the particular subarea, for example the particular ward, such that all medical devices 31, 32 located within such subarea apply the same configuration and drug library settings.

Figure 9:
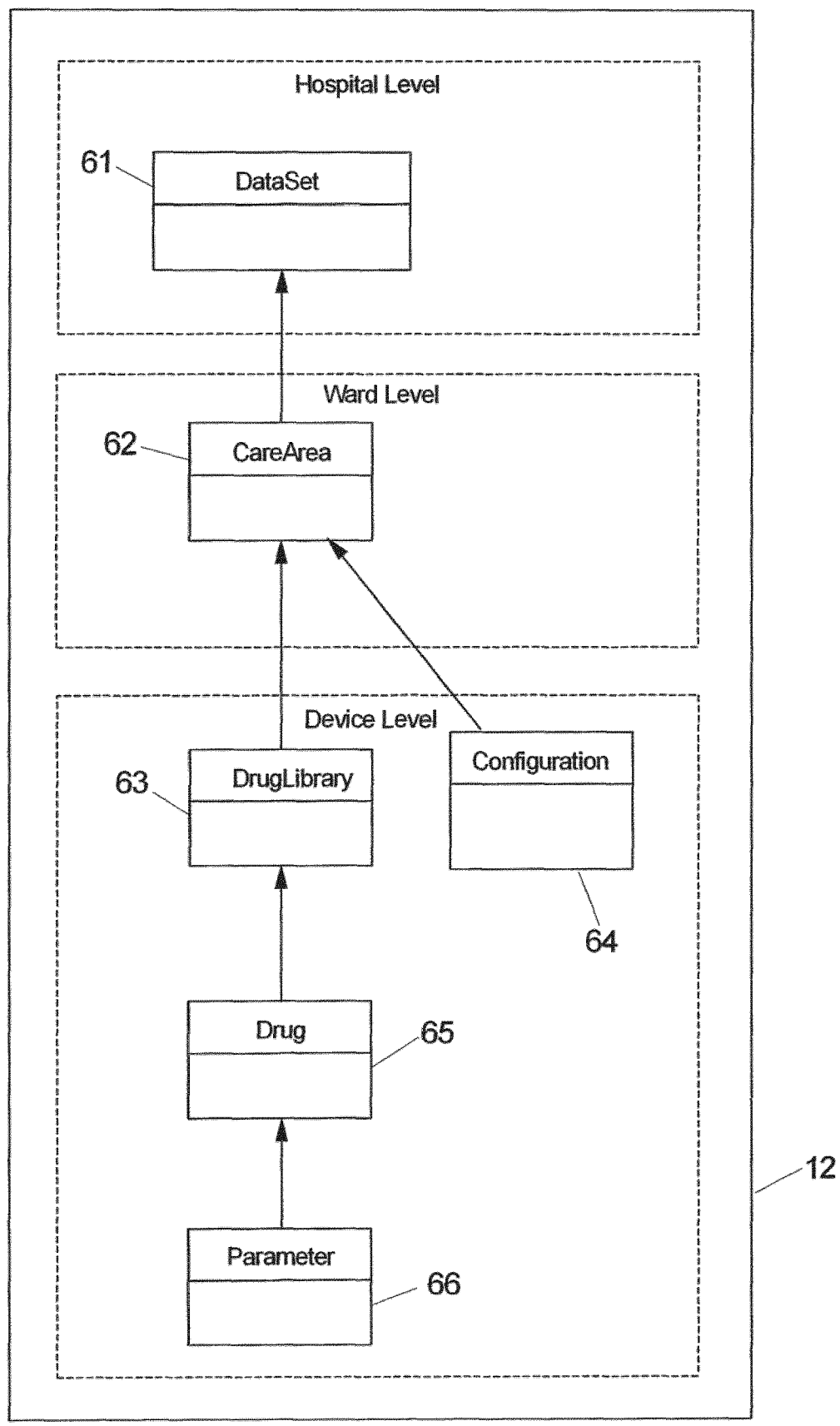
FIG. 9 shows a schematic overview of a data set composition within a web based service for providing drug library data.

Various care areas furthermore may be grouped to form a data set representing the structure of the entire healthcare environment 3, for example the entire hospital. The composition of a data set is shown in FIG. 9. In this particular example on a hospital level one data set exists (G1) to which up to 19 care areas may belong (G2). The care areas herein represent a ward level and are related to different wards or departments of the hospital (G2). On a device level one drug library (G3) and one configuration (G4) are associated with each care area, wherein the drug library contains data on drugs (G5) and parameters for its administration (G6).

Figure 10:
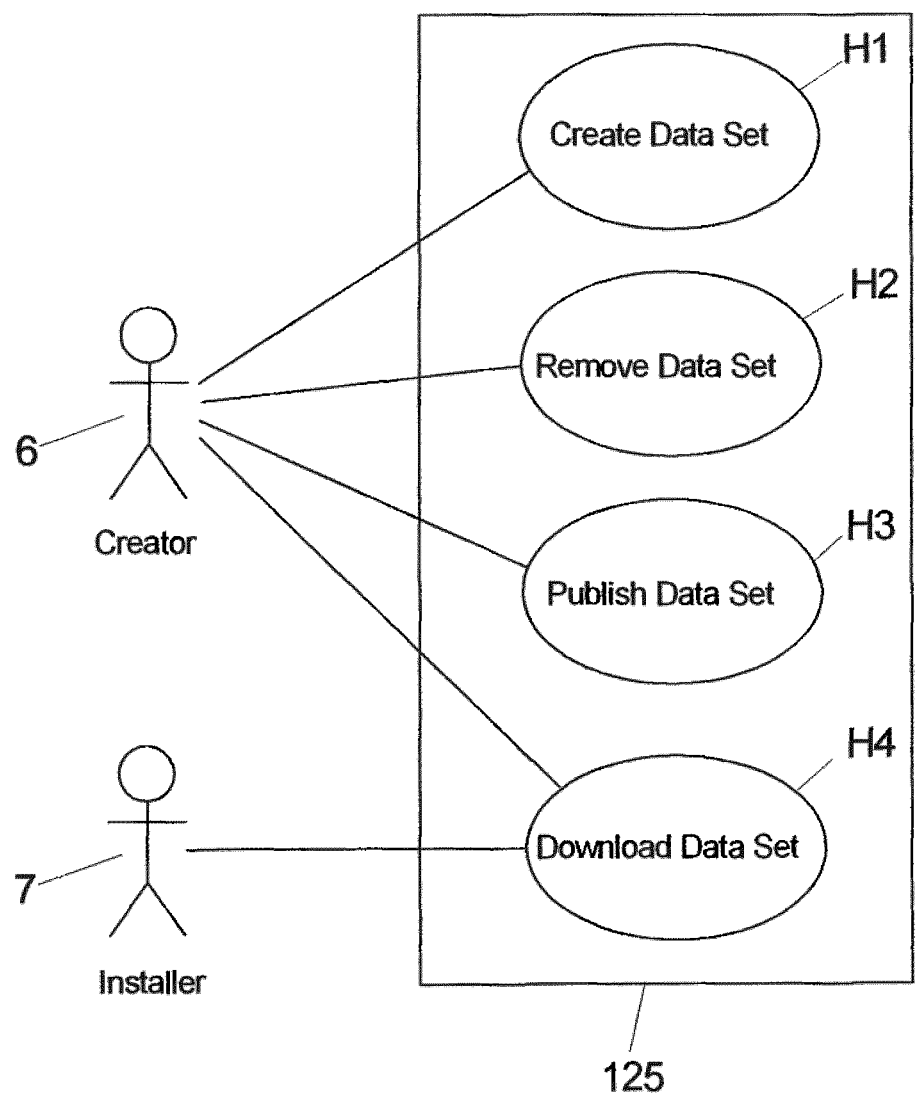
FIG. 10 shows a schematic overview of a data set creation within a web based service for providing drug library data.

As shown in FIG. 9, on a hospital facility level only one data set (G1) may exist mapping the structure of the entire hospital, although a user may be allowed to create, edit and share multiple data sets. As shown in FIG. 10, a user 6 may create a data set (H1), may remove a data set (H2), may publish a data set (H3) and may download a data set (H4). Furthermore, an installer 7 different than the user (creator) 6 may download a data set without being able to edit it in order to install the data set within a healthcare environment 3.

Figure 11:
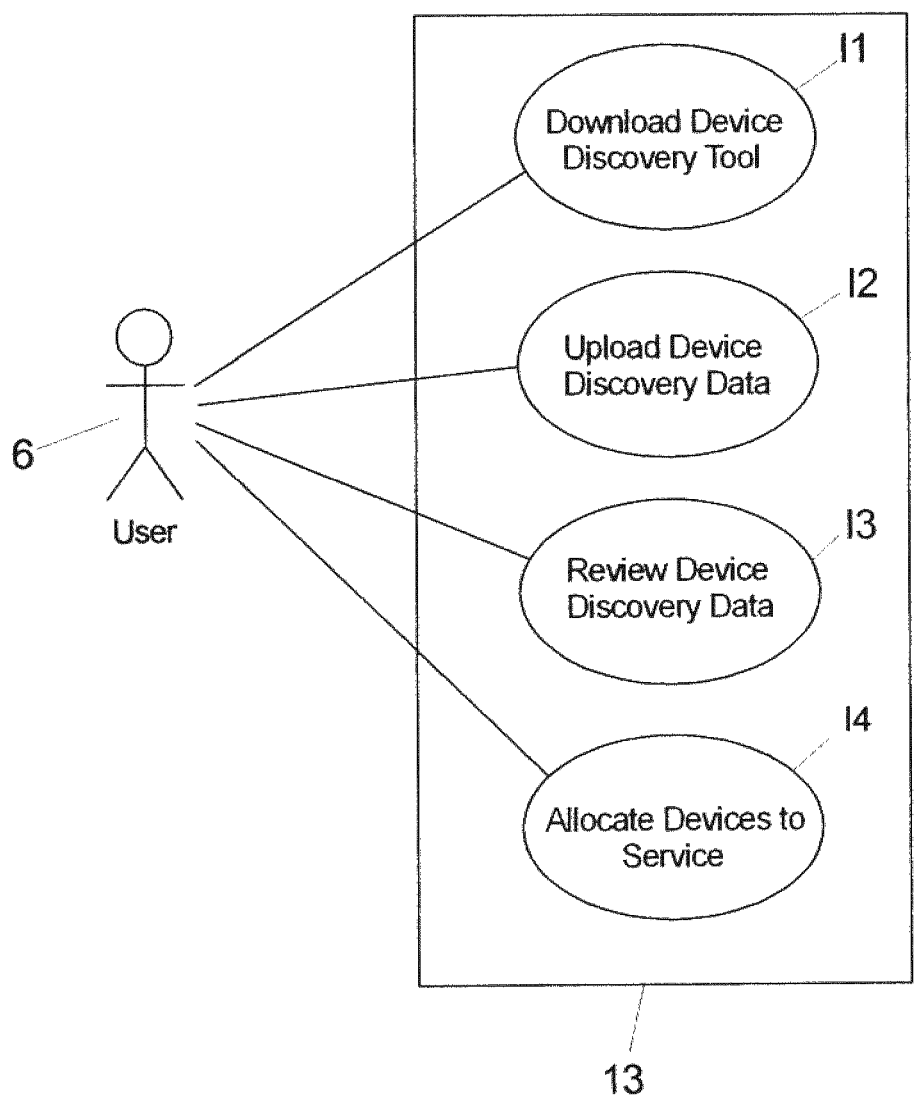
FIG. 11 shows a schematic overview of a functionality of a device discovery tool to be used in connection with a web based service for providing drug library data.

The web based service operates outside of the healthcare environment domain. The web based service therefore provides tools to users for download which facilitate to gather information about the installation of medical devices 31, 32 within a particular healthcare environment 3 such as a hospital. In particular, a user 6 may, as shown in FIG. 11, download a device discovery tool (11) which serves to gather data allowing for a localization of medical devices 31, 32 within a particular healthcare environment 3. As shown in FIG. 11, a user 6 may furthermore upload device discovery data to the drug library server 1 after executing the device discovery tool within a healthcare environment 3

(12), may review device discovery data (13) and may allocate medical devices 31, 32 to a service (14).

The device discovery tool is executed, after download, on a communication device 41 within a particular healthcare environment 3 (see FIG. 1). The device discovery tool herein may be used to search the local network 33 of the healthcare environment 3 for racks 31 serving as communication spines for infusion pumps 32 and may extract data from log files of the racks 31 to obtain data on the infusion pumps 32 connected to the rack 31 currently or previously. In this regard, each connection of an infusion pump 32 to a rack 31 may log a message in the log file of the rack 31 containing the serial/product number of the infusion pump 32. This data may be extracted by the device discovery tool to provide information on the use of infusion pumps 32 within a healthcare environment 3. The data extracted from the log files may be combined with localization data stored within the rack 31 having being set previously by web interface parameter settings. The result data extracted, across all racks 31 on the network 33, is then uploaded to the drug library server 1, in particular a client space of a user on the drug library server 1, for further analysis.

Figure 12:
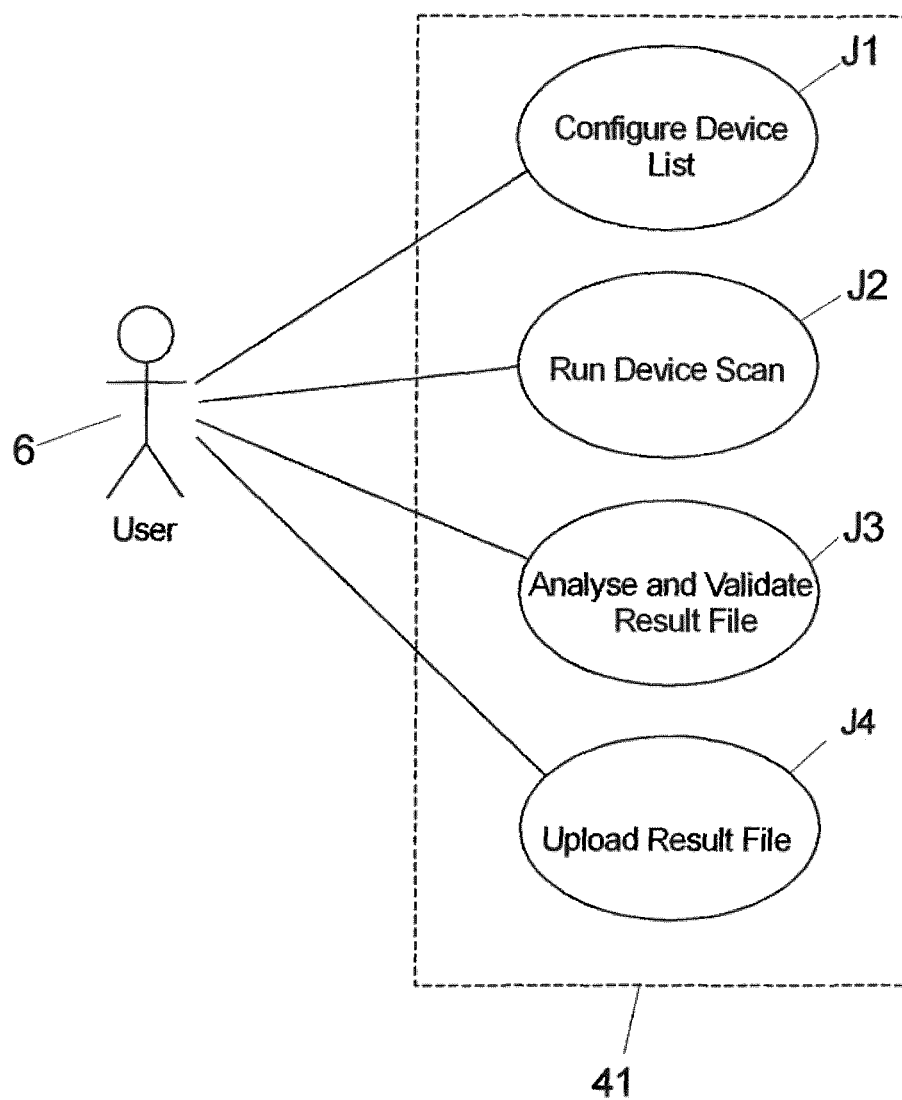
FIG. 12 shows a schematic overview of a functionality of the device discovery tool to allocate medical devices in a local network.

As shown in FIG. 12, a user 6, in the context of the device discovery tool installed for example on the distribution server 34 within the healthcare environment 3 (see FIG. 1), may configure a device list listing medical devices 31, 32 (J1), may run a device scan (J2), may analyze and validate a result file (J3) and may upload the result file to the drug library server 1 (J4).

By means of the device discovery tool localization information can be associated to medical devices 31, 32 and their movement in a care unit or a hospital. This information may be used to map a structure of the hospital for example by listing all medical devices 31, 32 allocated to a service and their range of movement.

Furthermore, a care area may be automatically assigned to a particular medical device 31, 32 dependent on its location in the healthcare environment 3. For example, an infusion pump 32 attached to a rack 31 in a particular bedroom in a ward in a care unit may automatically prompt a particular care area mapped to this location.

Figure 13:
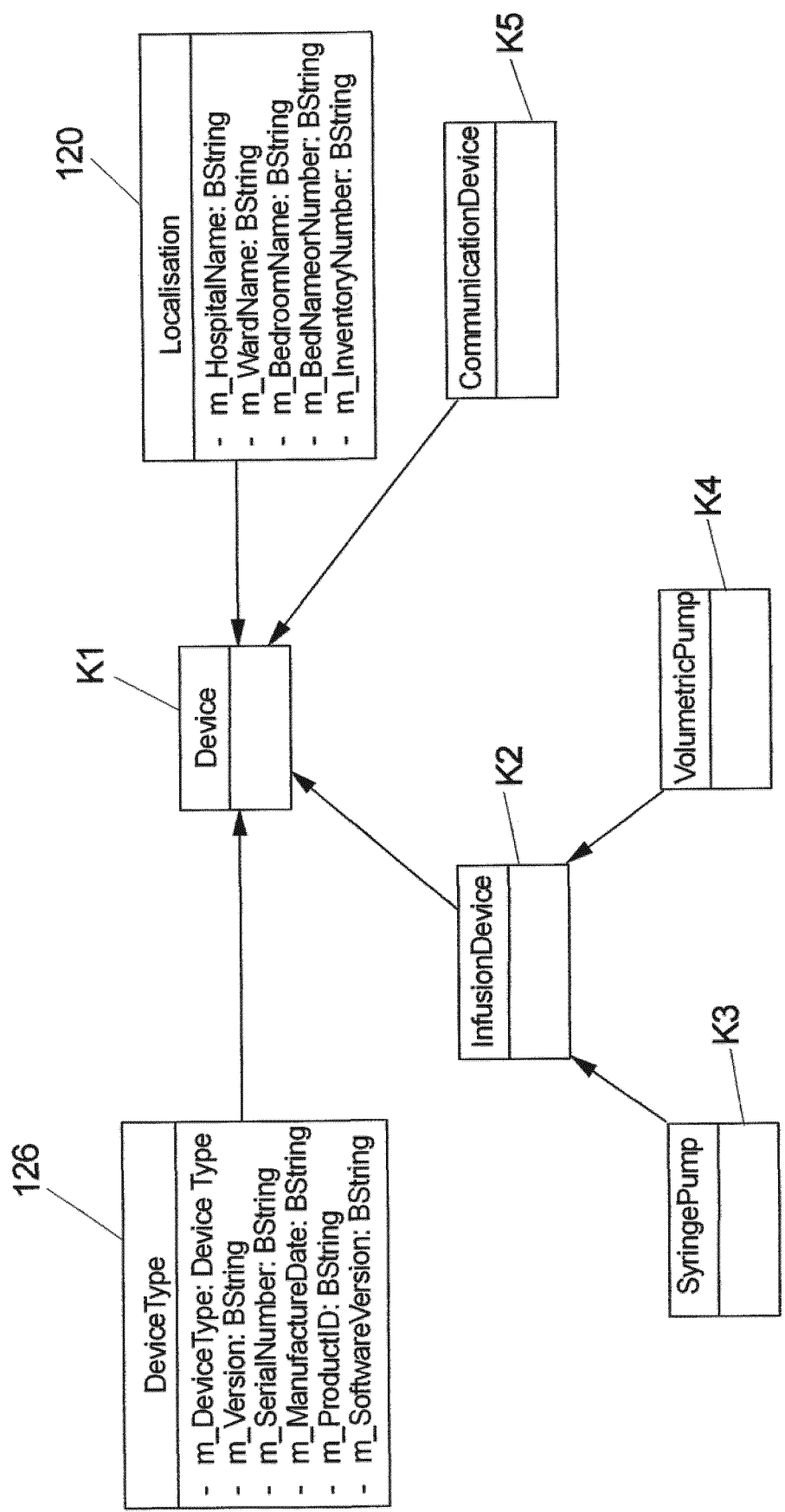
FIG. 13 shows a schematic overview of medical devices and their classification within a web based service for providing drug library data.

As shown in FIG. 13, medical devices 31, 32 may be categorized. A top category herein contains all devices (K1). Such devices may be then categorized as infusion devices (K2) and communication devices (K5) such as racks 31 serving as communication links for infusion devices 32 attached to it. The infusion devices (K2) may further be categorized into syringe pumps (K3) and volumetric pumps (K4). Further subcategories may exist relating to particular infusion device products of particular manufacturers. Device data can be accessed via the data base components interface 12 of the drug library server 1. In particular, medical devices 31, 32 may be specified in a device profile database 126 (see FIG. 2) and may contain data on the device type, a version, a serial number, a manufacturing date, a product ID and a software version. Furthermore, data on the localization of medical devices 31, 32 in a healthcare environment 3 are stored in a device localization data base containing data on the hospital facility name, the care unit name, the ward name, the bedroom name, the bed name or number and the inventory number, thus specifying the exact location of medical devices 31, 32 within a hospital.

A device manager or inventory manager may be used to generate a static barcode or to record a static barcode (generated using an external tool) in order to attach the barcode to a device 31, 32. The device manager for example additionally includes a device discovery tool to automatically record medical devices 31, 32 connected to the hospital local network 33 (for example a local area network). The device discovery tool may also be used to generate a barcode to be attached to a medical device 31, 32. Barcodes in this regard can be attributed to racks 31 or infusion pumps 32 and may serve to establish a link to a web interface associated with the rack 31 or the infusion pump 32. Such barcodes may for example be provided as so called QR codes that may be scanned by a barcode reader directly linked to a rack 31 or an infusion pump 32, a smart barcode reader or a communication device 40, 41 such as a PDA (smart device) or another mobile device. The barcode may for example contain a unique identifier such as a host name, a MAC address or a static IP address allowing for establishing a communication link to a web interface associated with the respective medical device 31, 32.

Figure 14:
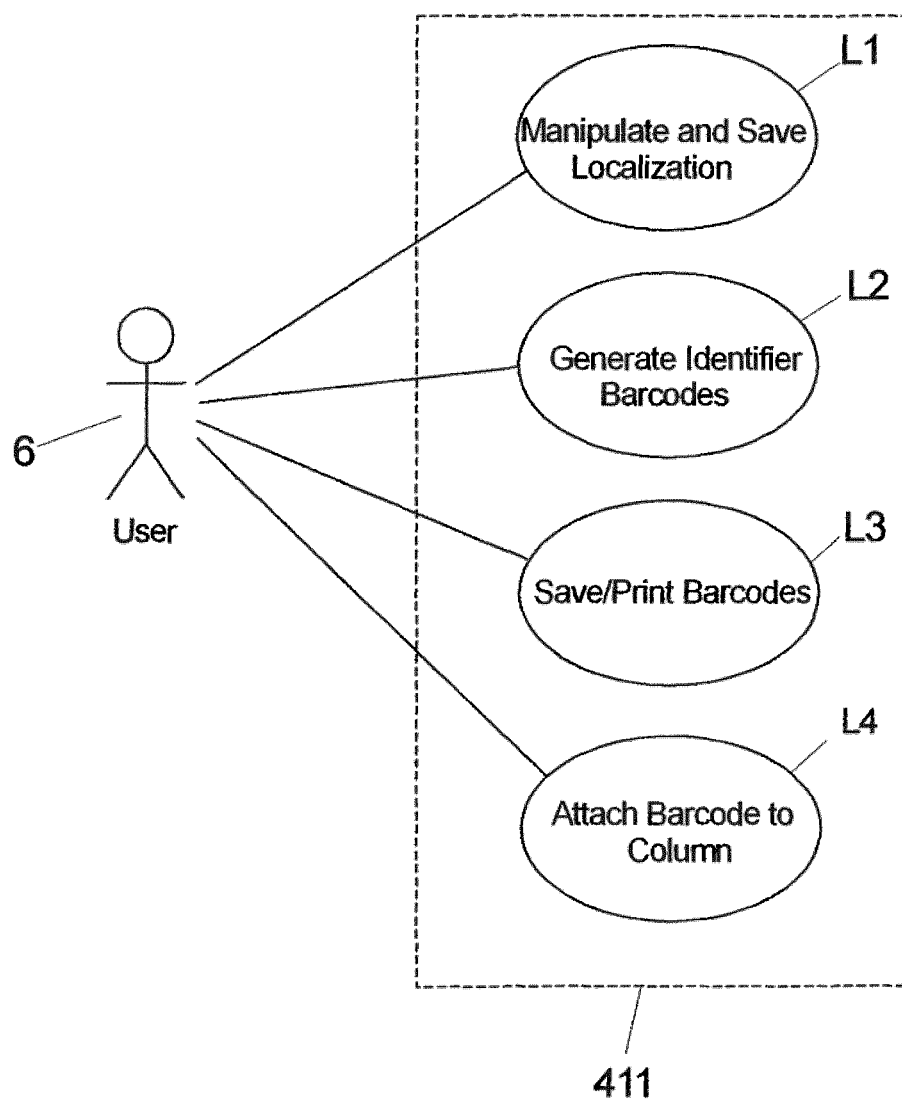
FIG. 14 shows a schematic overview of a functionality of a device discovery tool facilitating the generation of a barcode for identifying a medical device and to be attached to the medical device.

As shown in FIG. 14, a user 6, by means of the device discovery tool, may manipulate and save a localization of a particular medical device 31, 32, for example after a device scan has been performed (L1). Once the localization of the medical device 31, 32 is set including a unique identifier such as a host name or a static IP address linking the medical device 31, 32 with its associated web interface, a barcode may be generated (L2), saved and printed (L3) and attached to the respective medical device 31, 32 (L4).

Figure 15:
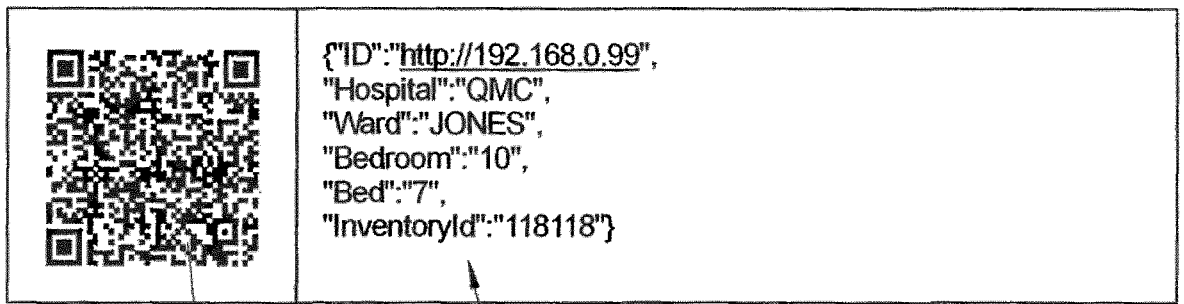
FIG. 15 shows an example of a barcode.

An example of such a barcode 8 is shown in FIG. 15. The barcode 8 in this particular example encodes the data shown to the right including a unique identifier in the shape of a static IP address, a hospital name, a ward name, a bedroom number, a bed number and an inventory ID. A scan of the barcode 8 by means of a communication device 40, 41 such as a portable device (for example a mobile phone, a PDA, a tablet PC or the like) leads to a displaying of the information contained in the barcode 8 on the display of the portable device. Tapping the display of the portable device (if the portable device comprises a touch screen) then takes the user 6 to the web interface of the respective medical device 31, 32, provided the portable device is on the hospital local network 33.

A barcode 8 can also be displayed directly on a screen of a medical device 31, 32. In this case the barcode 8 may be static or dynamic. In case of a static barcode, the barcode values are set by a specific tool in a medical device 31, 32 in accordance with a device manager. In case of a static barcode, the device manager stores information using a unique identifier identifying the medical device 31, 32 (for example serial number or MAC Address) and the related barcode. In case of a dynamic barcode, the barcode 8 may be generated directly by the medical device 31, 32 (for example by using a unique identifier and timestamp, or by means of a random generator) or by the distribution server 34. In the latter case the distribution server 34 is responsible of keeping track of the unique identifier of a medical device 31, 32 in an associated barcode 8.

By accessing the web interface of a medical device 31, 32 settings of the medical device 31, 32 may be edited. In addition, by accessing the web interface drug library data obtained from the distribution server 34 can be transferred to the medical device 31, 32 in order to install the data on the medical device 31, 32.

Figure 16:
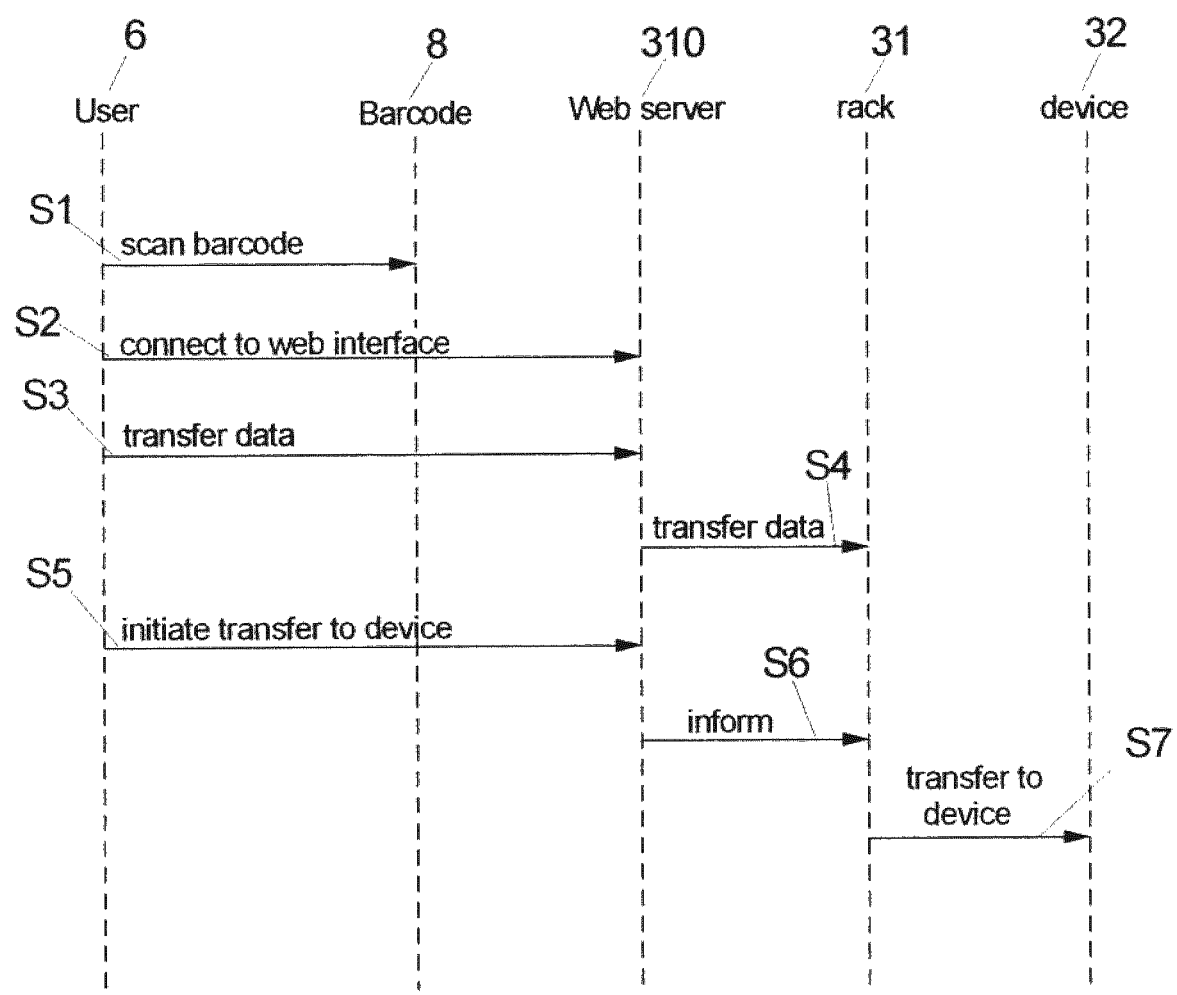
FIG. 16 shows a schematic sequence diagram for transferring drug library data to a medical device.

For this, in a first step, a certain drug library is downloaded by a user 6 to a communication device 40, 41 such as a portable device, possibly after a notification of a newly published data set, a care area, a drug library or a configuration. Once the user 6 has downloaded the data to the communication device 40, 41, the user 6 transfers the data to the medical device 31, 32 using a sequence as shown in FIG. 16. Herein, first the user 6 scans the barcode 8 on the medical device 31, 32 to which the data shall be transferred, in this particular example a barcode 8 on a rack 31 (step S1). Upon scanning of the barcode 8 the user 6 is directed to the web interface of the rack 31 (step S2) and, by means of the web interface, transfers the data to the rack 31 (step S3). Once the data is transferred to the rack 31 via a communication interface 310 such as a web server installed on the rack 31 (step S4), the user 6 may initiate a distribution of the data to infusion devices 32 attached to the rack 31 by inputting a respective command via the communication interface 310, which then informs the rack 31 accordingly (steps S5, S6 and S7).

By using this sequence it can be made sure that drug library data is not transferred to infusion pumps 32 while the infusion pumps 32 are in the process of infusing drugs to patients. For this, the user 6 first downloads the data to be installed to his communication device 40, 41 and then transfers the data, via the rack 31, to the respective infusion devices 32.

It however is also possible to directly transfer data from the drug library server 1 to medical devices 31, 32, without taking a detour via a separate communication device 40, 41 such as a portable device, for example a PDA or a mobile phone.

Alternatively, for example, an internal distribution server 34 as shown in FIG. 1 may be located within the healthcare environment 3 and may be connected to the local network 33. The internal distribution server 34 serves to download drug library data from the drug library server 1 whenever new drug library data, for example, a newly published data set, a care area, a drug library or a configuration or the like is available at the drug library server 1.

The internal distribution server 34 comprises a list of all medical devices 31, 32 such as racks 31 and infusion devices 32 located within the healthcare environment 3. Whenever a medical device such as an infusion device 32 is connected to the local network 33, the internal distribution server 34 verifies the medical device against its pre-stored list of devices and checks the version of data currently installed on the medical device 31, 32 and its compatibility with the newly published data. If the newly published data is compatible with the medical device 31, 32, the internal distribution server 34 transfers the data to the medical device 31, 32 upon connection of the medical device 31, 32 to the local network 30 and logs the transaction.

The use of an internal distribution server 34 has the advantage that the transferral of data to the medical devices 31, 32 can take place automatically without the need for additional steps involving a communication device 40, 41. The process is transparent for a user and involves minimum user interaction.

Additionally, the internal distribution server 34 may comprise a web server installed on the internal distribution server 34. The web server may be constituted to communicate and relay information about the status of transactions relating to particular medical devices 31, 32. The web server requires a clearly defined list of medical devices 31, 32 installed within the healthcare environment 3 and is enabled to communicate to a user for example versions of drug libraries currently installed on the medical devices 31, 32.

The idea of the invention is not limited to the embodiments described above.

By means of a web-based service provided via a drug library server of the kind described above located in the public domain, for example on the internet, it becomes possible to easily distribute and share drug library data within a particular healthcare environment, for example a hospital, and even a across separate healthcare environments, for example different hospitals.

By outputting drug library data in a standardized format, such as an XML or JSON/BSON format, the web based service may function with medical devices of different manufacturers.

The data may for example be parameterized using existing definitions of parameterizing drugs, as for example known from the so called HL7/IHE representations and the HIBC barcoding standard for smart pumps/IV medication.

LIST OF REFERENCE NUMERALS

1 Drug library server
10 Web server
11 Communication interface (web interface components interface)
110 Web interface components
111 Downloadable tools
112 Device control
113 Device localization
12 Database components interface
120a Hospital group
120b Hospital
120c Ward
121 Client profiles
122 Configurations
123 Drug libraries
124 Care areas
125 Data sets
126 Device profiles,
13 Manufacturer tools
2 Public communication network
3 Healthcare environment
30 Interface
31 Medical device (rack)
310 Communication interface (web server)
32 Medical device (infusion pump)
33 Local network
34 Internal distribution server
40 Communication device (portable device)
400 Web client
41 Communication device (external device)
410 Web client
411 Device discovery tool
5 External services
50 External systems
51 Manufacturer services
6 User
7 Installer
8 Barcode
81 Information
A1-3, B1-3, C1-6, D1-4, Features
E1-4, F1-4, G1-6, H1-4,
I1-4, J1-4, K1-5, L1-4
S1-S7 Steps

The invention claimed is:

1. A system for providing drug library or configuration data to a medical device located within a healthcare environment, the system comprising:
   a non-public, private local network of the healthcare environment,
   at least one medical device for administering a drug to a patient, the at least one medical device being located in the healthcare environment on a rack having a physical location and connected to the local network, a drug library server connected to the local network of the healthcare environment via a public communication network and constituted to provide drug library data to the at least one medical device via the public communication network, wherein the drug library server cannot obtain information on medical devices connected to the non-public, private local network, and at least one communication device separate from the at least one medical device and from the drug library server comprising a web client for communicating with the drug library server via the public communication network, wherein the public communication network is the internet and the drug library server hosts a web server configured to provide for a data communication with the web client of the at least one communication device, wherein the drug library server is constituted to provide a device discovery tool for download via the public communication network to the at least one communication device, the device discovery tool being operative to gather information about the at least one medical device installed within the healthcare environment, wherein the at least one communication device is operative to operate the device discovery tool, after download via the public communication network, within a particular healthcare environment to gather information about medical devices being installed within the healthcare environment, wherein the device discovery tool is operative to extract information about infusion pumps being installed on a rack, including physical localization data of the rack as to in which room in a hospital facility the rack is installed, and to upload said information to the drug library server via the public communication network, wherein the drug library server is operative to analyze the uploaded information and to associate the uploaded information with localization data of the rack stored on the drug library server.

2. The system according to claim 1, wherein the system is constituted to allow a user, by means of the at least one communication device, to access the drug library server via the public communication network in order to create and share a drug library, the drug library containing data relating to drugs to be administered to a patient by means of the at least one medical device, and/or create and share a configuration, the configuration defining operational rules of the at least one medical device, and/or create and share a care area, wherein the care area corresponds to a combination of a configuration and a drug library and is assigned to a subarea within the healthcare environment, and/or create and share a data set, the data set representing a group of care areas.

3. The system according to claim 1, wherein the device discovery tool searches the local network of the healthcare environment for medical devices connected to it.

4. The system according to claim 1, wherein based on localization data of the rack, a care area is assigned to the at least one medical device.

5. The system according to claim 1, wherein based on localization data of the rack obtained by means of the device discovery tool, a barcode identifying the at least one medical device is generated to be attached to the at least one medical device.

6. The system according to claim 1, further comprising a communication device located within the healthcare environment operative to scan a barcode attached to the at least one medical device and identifying the at least one medical device in order to access a communication interface of the at least one medical device.

7. The system according to claim 1, wherein for installing drug library data on the at least one medical device, the drug library data is downloaded from the drug library server to at least one communication device and transferred from the at least one communication device to the at least one medical device.

8. The system according to claim 7, wherein for transferring the drug library data from the at least one communication device to the at least one medical device, a barcode of the at least one medical device is scanned by means of the at least one communication device, a communication interface of the at least one medical device is accessed and the drug library data is transferred to the at least one medical device.

9. The system according to claim 1, wherein for installing drug library data on the at least one medical device, the drug library data is downloaded from the drug library server to an internal distribution server located within the local network of the healthcare environment and transferred from the internal distribution server to the at least one medical device.

10. The system according to claim 1, wherein the drug library server is constituted to output drug library data in an XML or JSON/BSON format.

11. A method for providing drug library data to a medical device located within a healthcare environment, the method comprising:

installing drug library data on at least one medical device for administering a drug to a patient, the at least one medical device being located in a healthcare environment on a rack having a physical location and connected to a non-public, private local network of the healthcare environment, wherein the drug library data is provided to the at least one medical device by a drug library server connected to the local network of the healthcare environment via a public communication network, wherein the drug library server is not able to communicate with medical devices connected to the non-public, private local network and cannot obtain information on medical devices connected to the non-public, private local network wherein at least one communication device, separate from the at least one medical device and the drug library service and using a web client, communicates with the drug library server via the public communication network, wherein the public communication network is the internet and the drug library server hosts a web server configured to provide for a data communication with the web client of the at least one communication device, wherein the drug library server provides a device discovery tool for download via the public communication network to the at least one communication device, the device discovery tool being operative to gather information about the at least one medical device installed within the healthcare environment, wherein the at least one communication device operates the device discovery tool, after download via the public communication network, within a particular healthcare environment to gather information about medical devices being installed within the healthcare environment, wherein the device discovery tool extracts information about infusion pumps being installed on a rack, including physical localization data of the rackas to in which room in a hospital facility the rack is installed, and uploads said information to the drug library server via the public communication network,
wherein the drug library server analyzes the uploaded information and associates the uploaded information with localization data of the rack stored on the drug library server.

\* \* \* \* \*